(12) United States Patent
Brcka

(10) Patent No.: US 7,556,718 B2
(45) Date of Patent: Jul. 7, 2009

(54) HIGHLY IONIZED PVD WITH MOVING MAGNETIC FIELD ENVELOPE FOR UNIFORM COVERAGE OF FEATURE STRUCTURE AND WAFER

(75) Inventor: Jozef Brcka, Gilbert, AZ (US)

(73) Assignee: Tokyo Electron Limited, Tokyo (JP)

( * ) Notice: Subject to any disclaimer, the term of this patent is extended or adjusted under 35 U.S.C. 154(b) by 771 days.

(21) Appl. No.: 10/873,908

(22) Filed: Jun. 22, 2004

(65) Prior Publication Data
US 2005/0279624 A1 Dec. 22, 2005

(51) Int. Cl.
C23C 14/00 (2006.01)
C25B 11/00 (2006.01)
C25B 13/00 (2006.01)

(52) U.S. Cl. .............. 204/192.13; 204/192.1; 204/298.01; 204/298.16; 204/298.2; 204/298.22; 204/298.31; 204/298.37

(58) Field of Classification Search ............ 204/192.12, 204/192.15, 192.17, 192.3, 298.09, 298.18
See application file for complete search history.

(56) References Cited

U.S. PATENT DOCUMENTS

| | | | | |
|---|---|---|---|---|
| 4,810,347 A | * | 3/1989 | Smith | 204/298.18 |
| 4,842,703 A | * | 6/1989 | Class et al. | 204/192.12 |
| 4,999,096 A | | 3/1991 | Nihei et al. | |
| 5,130,005 A | | 7/1992 | Hurwitt et al. | |
| 5,280,219 A | | 1/1994 | Ghanbari | |
| 5,855,744 A | * | 1/1999 | Halsey et al. | 204/192.12 |
| 6,042,700 A | * | 3/2000 | Gopalraja et al. | 204/192.15 |
| 6,080,287 A | | 6/2000 | Drewery et al. | |
| 6,100,200 A | | 8/2000 | Van Buskirk et al. | |
| 6,132,564 A | | 10/2000 | Licata | |
| 6,197,165 B1 | | 3/2001 | Drewery et al. | |
| 6,224,724 B1 | * | 5/2001 | Licata et al. | 204/298.06 |
| 6,274,008 B1 | | 8/2001 | Gopalraja et al. | |
| 6,287,435 B1 | | 9/2001 | Drewery et al. | |
| 6,793,785 B2 | | 9/2004 | Teng et al. | |

(Continued)

FOREIGN PATENT DOCUMENTS

TW 421819 B 2/2001
TW 574407 B 2/2004

(Continued)

Primary Examiner—Patrick Ryan
Assistant Examiner—Michael Band
(74) Attorney, Agent, or Firm—Wood, Herron & Evans, L.L.P.

(57) ABSTRACT

This invention relates to ionized PVD processing of semiconductor wafers and provides conditions for highly uniform deposition-etch process sequence and coverage capabilities of high aspect ratio (HAR) features within a single processing chamber. A plasma is generated and maintained by an inductively coupled plasma (ICP) source. A deposition process step is performed in which metal vapor is produced from a target of a PVD source. Location and sputter efficiency at the target surface is enhanced by moving a magnet pack to create a traveling or sweeping magnetic field envelope. The target is energized from a DC power supply and pressures effective for an efficient thermalization of the sputtered atoms ($30<p<100$ mTorr) are maintained in the chamber during deposition. A uniform thickness of the metal on the wafer is produced within each magnet sweeping cycle. Magnetic field localization using an annular sweeping motion over the entire target surface generates conditions for reasonable deposition rates, high target utilization, high ionization of the metal atoms, uniform flat field deposition and etching, and nearly identical conditions for HAR feature coverage at the center and edge of the wafer.

19 Claims, 11 Drawing Sheets

U.S. PATENT DOCUMENTS

2003/0034244 A1 2/2003 Yasar et al.
2004/0028837 A1 2/2004 Fink
2004/0188239 A1 9/2004 Robison et al.

FOREIGN PATENT DOCUMENTS

WO 02/11176 A1 2/2002
WO 03/025971 A2 3/2003

* cited by examiner

HIGHLY IONIZED PVD WITH MOVING MAGNETIC FIELD ENVELOPE FOR UNIFORM COVERAGE OF FEATURE STRUCTURE AND WAFER

This application is related to U.S. patent application Ser. No. 10/795,093, filed Mar. 5, 2004, which is a continuation-in-part of U.S. patent application Ser. No. 10/138,049 filed May 3, 2002, which claims priority to U.S. Provisional Patent Application Ser. No. 60/288,952, filed May 4, 2001, each hereby expressly incorporated herein by reference.

FIELD OF THE INVENTION

This invention relates to the metallization of via and trench structures on semiconductor wafers. More particularly, the invention relates to the metallization of high aspect ratio via and trench structures of silicon wafers utilizing ionized sputtered materials to form barrier and seed layers.

BACKGROUND OF THE INVENTION

Ionized PVD has been utilized in semiconductor processing for metallization and interconnects, and appears promising for extension to submicron technology. In the metallization of high aspect ratio (HAR) via holes and trenches on semiconductor wafers, it has been considered important that the barrier layer and the seed layer have good sidewall and bottom coverage across the wafer. Ionized PVD deposition is used for barrier and seed layer metallization in advanced integrated circuit (IC) wafers, and has provided good sidewall and bottom coverage in via and trench structures. Requirements nonetheless become more critical as the geometries shrink and as the via dimensions go below 0.15 micrometers.

It is highly desirable to have an ionized PVD process where bottom and sidewall coverage are well balanced and overhang is minimized when features are small. To achieve this, the sequential deposition and etch processes have been proposed previously in U.S. Pat. No. 6,100,200 (Van Buskirk, et al.), however, at described temperatures the process would result in total agglomeration of Cu seed layers, overhang and closure of via and trenches with large islands of Cu and discontinuous Cu layers. Reduced temperature requires low power sputtering conditions that would put severe deposition rate and throughput limitations on such a process. Another limitation would occur when processing wafers in independent deposition and etch systems. Transferring the wafer between an etch chamber to a separate deposition chamber or between an etch station to a distinct deposition station within the same module has disadvantages both from cost-of-process and quality-of-process points of view.

In U.S. Pat. No. 4,999,096 (Nikei, et al.) a method of and apparatus for sputtering by sequential deposition and etching in the same chamber is disclosed. However, this configuration has a significant disadvantage in that the internal coil is a source of contamination of the film being deposited or etched on the substrate. Furthermore, the suggestions of Nikei, et al., would result in non-uniform plasma generation and non-uniform etching of the substrate, and in the sequential etching and deposition process, both steps are not uniform across the wafer so as to result in a uniformly processed wafer at the end of the process.

U.S. Pat. No. 6,274,008 discusses an integrated copper fill process where a simultaneous clean-deposit step is carried out, using copper ions to clean and/or etch the bottom of via structures before the copper seed layer is deposited.

Accordingly, there is a need in iPVD particularly to improve barrier layer and seed layer sidewall and bottom coverage across the wafer, particularly where feature dimensions are below 0.15 micrometers.

SUMMARY OF THE INVENTION

An objective of the present invention is to provide for the metallization of interconnects and other deposition onto substrates having submicron high aspect ratio features.

Another objective of the present invention is to generate and control plasma that will contribute to the uniform plasma processing in deposition and/or etching sequence required for coverage of high aspect ratio features by ionized PVD, particularly at 300 mm wafers.

A still further objective of the present invention is to provide an increased metal ionization without additional increasing of the ICP power or DC power at the target.

Yet another objective of the invention is to provide azimuthally symmetric plasma and flexibility to control and compensate for any azimuthal nonuniformity that could be generated by interaction of the static magnetic field and an ICP source.

According to principles of the present invention, an ionized physical deposition method is provided that includes sealing a substrate within a chamber of a processing apparatus and performing an alternating, sequential deposition-etch process to deposit a film of material from a sputtering target on surfaces of high aspect ratio submicron features on the substrate while sweeping over the sputtering target a magnetic field that produces relatively high plasma confinement over only a portion of the surface of the target.

Also according to principles of the invention, an apparatus is provided that is configured to deposit a film on surfaces of high aspect ratio submicron features on a substrate sealed within a chamber of the processing apparatus, while sweeping over a sputtering surface of the sputtering target a magnetic field that produces relatively high plasma confinement over only a portion of the surface of the target. The apparatus is particularly useful for, and may be provided in conjunction with the capability of performing an alternating, sequential deposition-etch process to deposit a film of material from the sputtering target.

Other principles of the invention are embodied in the various features of alternative embodiments of the apparatus and method. Such an embodiment may be operable to perform ionized physical vapor deposition on a substrate in a vacuum chamber over a pressure range of from approximately 1 mTorr to over 30 mTorr. The apparatus may have, for example, a sputtering target at one end of the chamber and a substrate support at the other end of the chamber, an ICP source operable to inductively coupling RF energy into a plasma in a process volume within the chamber to form a high density plasma therein, and a magnet pack behind the sputtering target configured to sweep a magnetic field over the surface of the sputtering target. A controller may be provided that is programmed to operate the apparatus sequentially, with a single substrate in the chamber, without opening the chamber, in a plurality of modes including a deposition mode, by sputtering material from a sputtering target into the plasma to ionize the material and depositing the material onto the substrate, and an etch mode, by etching material from the substrate with ions from the plasma, the modes being performed while sweeping the magnetic field over the surface of the sputtering target. The deposition mode may be carried out at pressures greater than 30 mTorr, and the etch mode at pressures less than 10 mTorr.

In certain embodiments of the invention, the magnet pack may be configured to produce a magnetic field that confines the plasma to only a portion of the sputtering surface of the target and to sweep the field by moving that portion over the said surface of the target. The magnet pack may be configured to facilitate a change of the size of the portion of the surface over which the magnetic field is so confined.

The permanent magnet pack may be, for example, mounted behind the sputtering target and configured to produce the magnetic field, with one or more actuators being provided to move the magnet pack, in response to the controller, to cause the field to sweep over the sputtering surface of the sputtering target. The magnet pack may include a plurality of moveable magnet sectors, with a plurality of actuators provided, one linked to each sector and operable to move the sectors to sweep the field over the sputtering surface of the sputtering target. Alternatively, magnet pack may in include an annular magnet assembly with one or more actuators linked to the magnet assembly and operable to move the magnet pack in a gyro-motion to cause the field to sweep over the sputtering surface of the sputtering target.

These and other objects and advantages of the present invention will be more readily apparent from the following detailed description of illustrated embodiments of the invention.

DETAILED DESCRIPTION OF THE ILLUSTRATED EMBODIMENTS OF THE INVENTION

Figure 1:
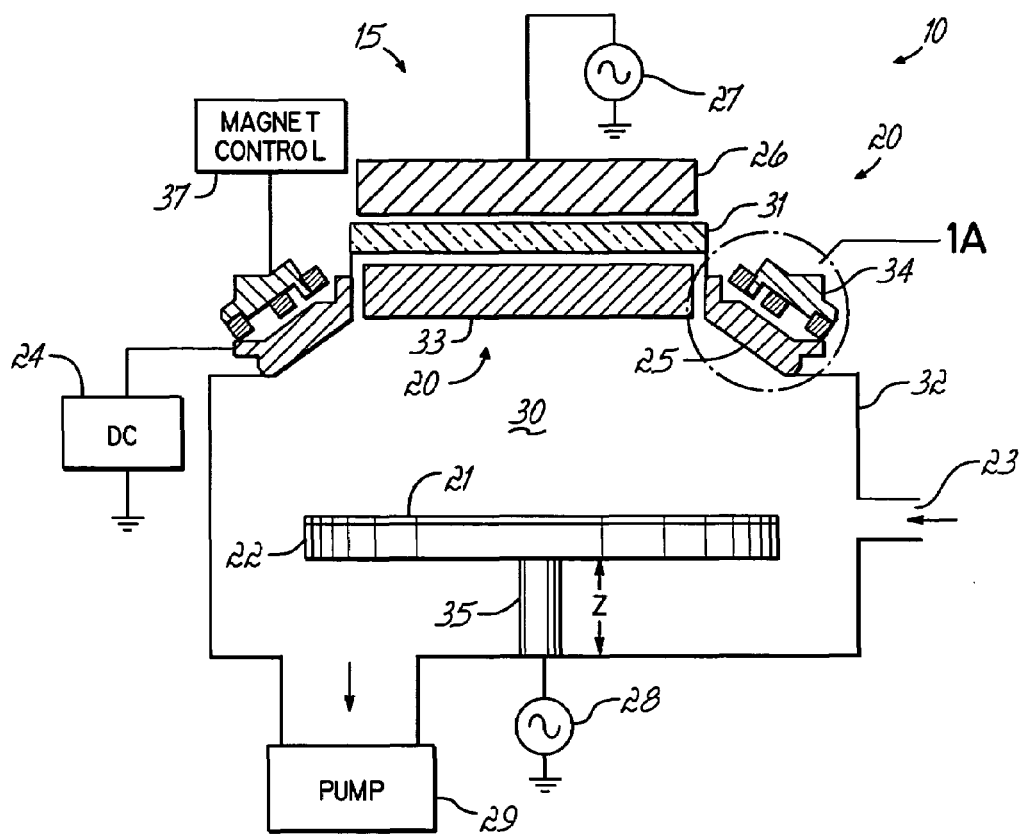
FIG. 1 is a diagrammatic cross-sectional representation of an iPVD apparatus for use according to principles of the present invention.

According to the invention in U.S. Pat. App. Publication No. 20030034244 (Yasar et al.), assigned to the same assignee as current application, a process and an apparatus are provided wherein sequential deposition and etching steps are used to solve problems set forth above. Application of that process may involve first depositing a thin layer of metallization, for example such as tantalum (Ta), tantalum nitride (TaN) or copper (Cu), and then, preferably after stopping the deposition, performing an ion etch step, preferably by ionized gas, for example such as argon (Ar). The etching step removes less material on both the field area on the top surface of the wafer and the via bottom than is deposited during the deposition step, and thus there is net deposition at the end of the process cycle. The deposition-etch cycle can be repeated as many times as needed to achieve a desired result. By balancing the deposition and etching times, rates and other deposition and etch parameters, overhang growth is eliminated or minimized, and overhang and bottom deposition is etched back and redistributed at least partially to the sidewalls.

In a deposition-etch process, the deposition can use an ionized physical vapor deposition (iPVD) process and apparatus having the features described in U.S. Pat. Nos. 6,287,435; 6,080,287; 6,197,165; and 6,132,564. These can be used for both the sequential deposition and etching processes. The sequential deposition-etch process can be applied to a substrate in the same process chamber without breaking vacuum or moving the wafer from chamber to chamber. The configuration of the apparatus allows rapid change from ionized PVD mode to an etching mode, or from an etching mode to an ionized PVD mode. The configuration of the apparatus also allows for instantaneous optimization of ionized-PVD process-control parameters during the deposition mode and of etching process-control parameters during the etching mode.

The consequence of these advantages is a high throughput of wafers with superior via metallization, and with a subsequent superior electroplated fill operation.

There are some constraints to utilizing an iPVD system at the maximum of its performance. For example, stable results can be achieved on 300 mm wafers in filling 0.1 micron via features within the central portion of the wafer, but filling such features near the edge of the wafer is more difficult. The present invention increases the ability of such existing hardware in optimizing uniformity for both processes quickly, both during deposition and etch modes. While an annular target of currently available hardware provides excellent conditions for flat field deposition uniformity, the present invention helps enable a large area ICP source to generate a large low pressure plasma for uniform etch process.

Moreover, a magnetic field produced by a magnet pack of the sputtering target has a tendency to create conditions for a domed plasma density due to peripheral confinement of the plasma. Further, an axially situated ICP source is optimal to ionize metal vapor sputtered from the target and fill features in the center of the wafer, but tends to generate an axially peaked high density plasma profile. With the present invention, the plasma can better provide a uniform etch sequence in a deposition-etch process as well as in a no-net-deposition (NND) process.

An NND process requires more strict conditions than does typical deposition-etch. For example, an NND process occurs at increased bias at the wafer so deposited metal (Ti for adhesion, Ta as a barrier and/or Cu as seed layer) is instantly removed from the flat field, from other horizontal surfaces like the top and bottom plane of the feature, while being deposited at the sidewalls of the feature. An NND process may be completed by deposition of the thin film at the bottom of the feature. The NND process benefits from fully identical nonuniformity distribution of the etch and deposition process, and from the highly uniform processes.

It is found that completely removing a magnet pack eliminates magnetic field confinement of the plasma at the target surface during an etch sequence, but can create an uncontrolled erosion profile at the target surface (low utilization and lifetime), a reduced deposition rate, and also effects like potential arcing, dark shield erosion, shallow angle deposition at the target surface and an increase in particles.

The configuration of the process module provided by the present invention produces a rotating, sweeping, or otherwise moving magnetic field envelope that results in an increase in the uniformity of an etch/deposition sequence and coverage at the wafer. Magnetic field localization and motion over the all target surface is better carried out in annular fashion, generating conditions for reasonable deposition rates, sustaining high target utilization, an optimal target erosion profile, higher ionization of the metal atoms, uniform flat field deposition and etching. It particularly creates optimal and identical conditions for HAR feature conformal via and trench coverage at both the center and edge of the wafer, and does so at high wafer throughput levels.

An iPVD apparatus 10 useful in accordance with the present invention is illustrated in FIG. 1. For ionized PVD, a wafer 21 is held in place on top of a temperature-controlled electrostatic chuck 22. Sputtering gas is supplied from a gas source 23 into a vacuum processing chamber 30, the pressure of which is maintained at a vacuum by pump 29 and adjusted to a proper ionized deposition range for iPVD. DC power is supplied from a power source 24 to an ionized material source 20 that includes a sputtering target 25 and an ICP source 15 that includes an antenna 26. RF power is supplied from an RF generator 27 of the ICP source 15. These electrical power sources 24 and 27 are turned on to power levels appropriate for the deposition by iPVD. The RF power 27 energizes a high-density inductively-coupled plasma in a process volume in the chamber 30 between the target 25 and the wafer 21.

Wafer RF bias is supplied to the chuck 22 by RF bias generator 28, which can also be turned on to a level appropriate during deposition to provide a net negative bias on the wafer 21 to improve and affect the process. The antenna 26 is positioned outside of the chamber 30 behind a dielectric window 31 in the chamber wall 32. A louvered deposition baffle 33, preferably formed of a slotted metallic material, is located inside of the chamber 30 closely spaced from the window 31 to shield the window 31 from deposition. A magnet pack 34 is located behind the target 25 to produce a magnetic tunnel over the target 25 for magnetron sputtering. A magnet control 37 is provided to change the magnet field strength between deposition and etch modes. This can include a magnet lift, rotation or other magnet movement mechanism for permanent magnets, when they are included in the magnet pack 34, or a magnet current control for electromagnets, when the magnet pack 34 employs electromagnets.

The temperature of the wafer 21 may be controlled to control via metallization, which may be accomplished by temperature heating or cooling elements (not shown) in the wafer table 22. The wafer table 22 may also be equipped with a Z-motion drive 35 to adjust the substrate-to-source distance to optimize deposition uniformity and the coverage and symmetry of the sidewalls and bottoms of the vias and other features on the substrate. Substrate-to-source distance can typically be 150 to 275 mm. Argon gas is the typical sputtering gas. To deposit a barrier layer of a metal nitride such as $TaN_x$, nitrogen gas, in addition to Argon gas, may be used during sputter deposition.

In the illustrated embodiments, an annular conical sputtering target 25 of the ionized physical vapor deposition (iPVD) apparatus 10 is enhanced and its erosion profile is controlled by the annular magnet pack 34 consisting of three annular rows of the magnets 34a, 34b and 34c of rectangular cross section, and an annular yoke 34d. The magnets and yoke are configured on a circle and oriented to generate magnetic fields parallel to the target surface and having null-B point 35e at the centerline of the annular target 25 close to the target-to-backplane boundary 34f.

With this arrangement, metal vapor flux from the target 25 is thermalized at an argon pressure that is higher than typical sputtering pressure, that is, is greater than about 30 mTorr. Usually, this pressure is less than 100 mTorr for argon gas, but for some applications and materials is higher, for example, 130 mTorr or 175 mTorr, etc. The ICP source 15, which is on the common axis of the target 25 and substrate holder 22, produces a high density plasma that in turn produces a high effective ionization of the metal in central area of the processing chamber 30 and above the wafer 21. Metal ions diffuse towards the wafer surface and are accelerated by bias voltage within the plasma sheath (that is, by the potential difference between plasma potential and wafer potential) at the wafer surface. A high density plasma may include, for example, plasmas having high $10^{12}$ e$^-$cm$^{-3}$, $10^{13}$ e$^-$cm$^{-3}$ or higher.

In a sequential deposition-etch procedure, the etch portion of the process requires conditions that differ from those of the deposition portion of the process, such as a pressure typically below 10 mTorr, with target sputtering turned off. The interaction of the magnetic field produced by the magnet pack 34, when that magnet pack is in position for assisting in the deposition process, typically reduces the etch uniformity and variable feature coverage across the wafer surface. The magnetron magnets are not needed for the etch process and can adversely interact with it.

Removal of the magnet pack bodily away from the plasma during etch steps can significantly reduce or eliminate interaction between the magnetic field and the etch process, and can provide at least a partial increase in etch and deposition uniformity. However, according to the present invention, eliminating the magnetic field only in a portion of the plasma environment, for example, azimuthally 25 to 75 percent, and providing a sweeping of the magnetic field envelope around or otherwise across the target surface, generates more advantages and benefits for a uniform deposition and etching process and for enhanced metal ionization, which has a direct consequence of better, more uniform feature coverage.

Figure 2:
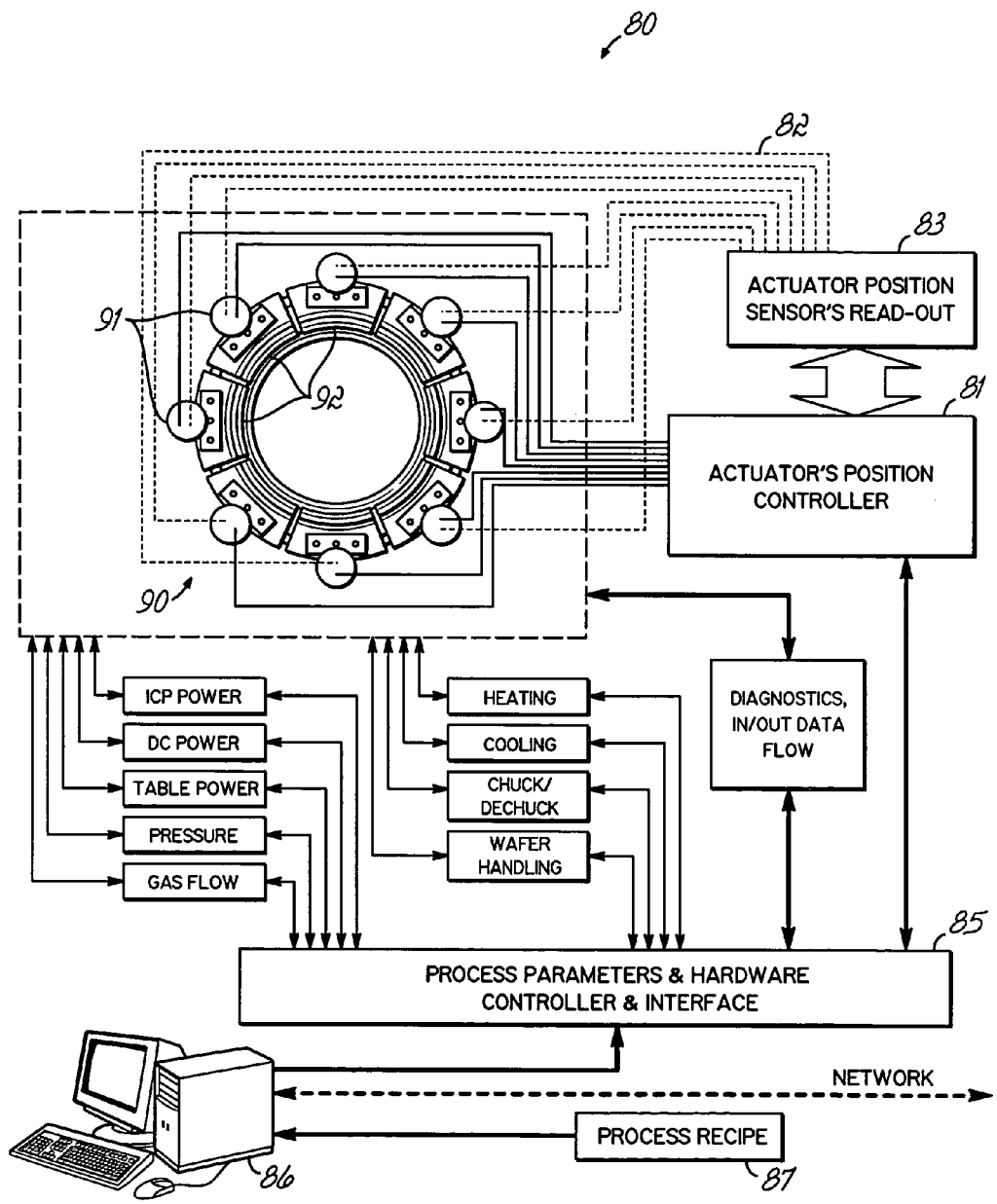
FIG. 2 is a simplified block diagram of the hardware and process control of an embodiment of the apparatus of FIG. 1.

The apparatus 10 includes a magnet pack motion control 80, which is schematically shown on FIG. 2. This includes an advanced magnet pack assembly 90 having an effective magnet pack configuration of the magnet pack 34, described above, which is integrated into the ionized PVD source 20. The magnet pack assembly 90 is made up of separate circumferential sections 92, shown as eight sections each spanning 45 degrees of an annulus. Individual actuators 91 are provided to individually move each of the sections 92. The actuators 91 are controlled by an actuator position controller 81 that has feedback control 82 to an actuator status reader unit 83. Both actuator motion controller 81 and sensor status unit 83 are controlled through a process parameter and hardware controller and interface unit 85, which is directed by a CPU 86 according to a recipe stored in a memory 87.

Figure 3:
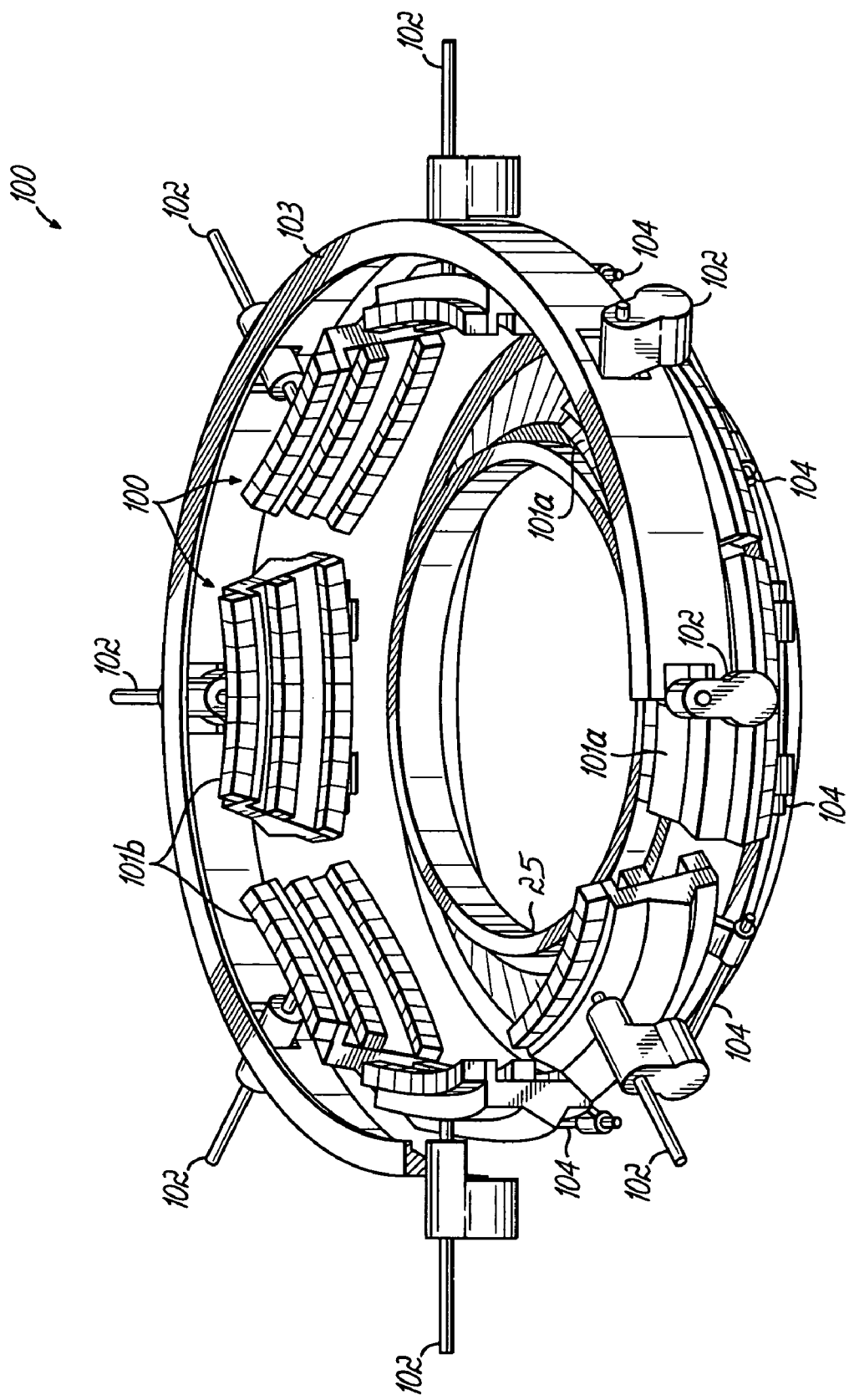
FIG. 3 is a disassembled perspective diagram, partially broken away, of a sectored annular magnet pack of FIG. 1A configured for providing a rotating magnetic envelope inside the chamber according to one embodiment of the present invention.
Figure 3A:
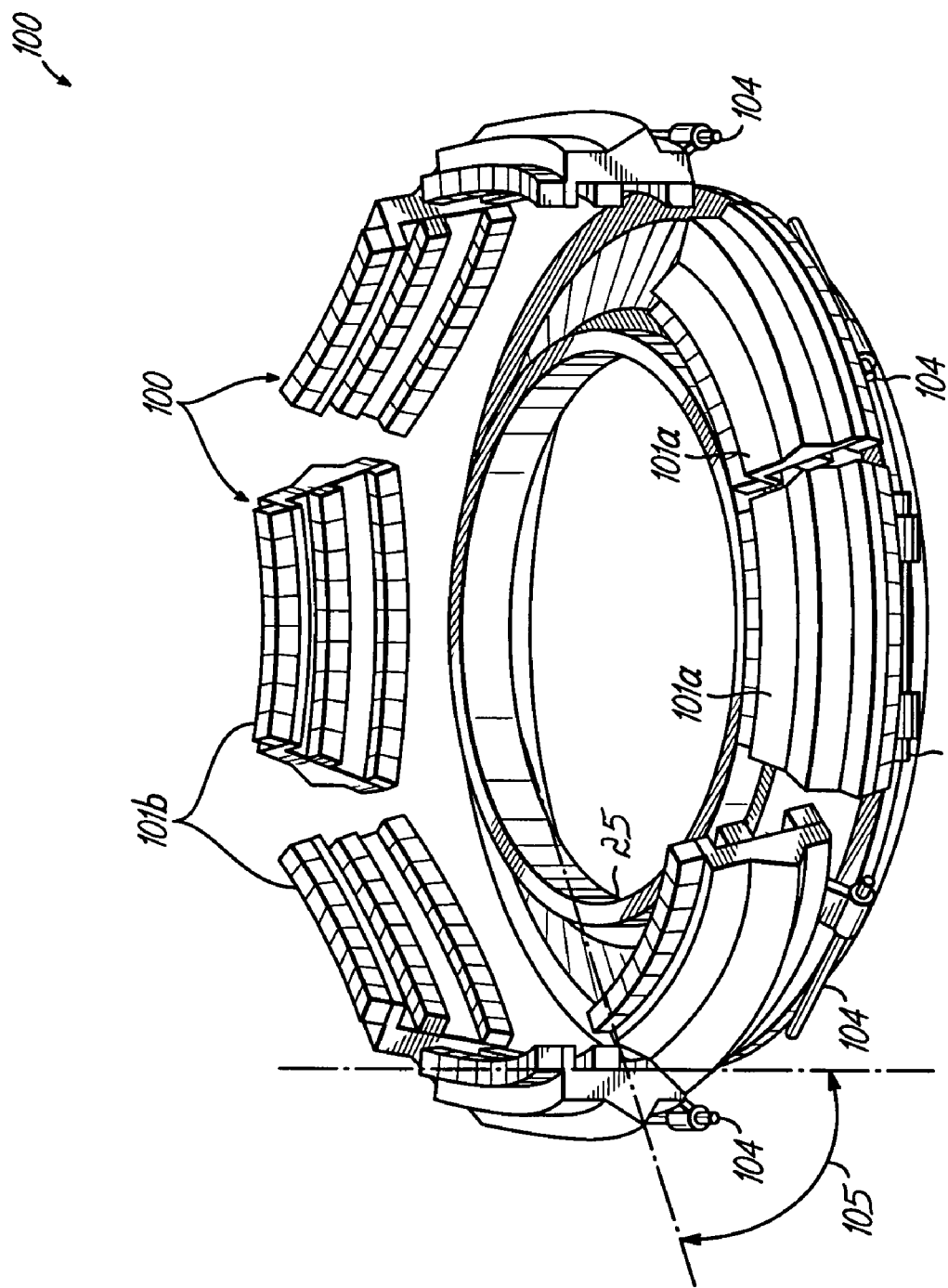
FIG. 3A is a further disassembled view of the magnet pack of FIG. 3.

FIGS. 3 and 3A illustrate an annular magnet pack 100, which is one embodiment of the magnet pack assembly 90 of FIG. 2 that is configured to create an off-axis magnetic field envelope. Annular magnet pack 100 is divided into independent sectors 101, from six to eight in number (eight as shown). Each sector 101 can rotate around a mounting axis 104 to an angle 105 with the back side of the target 25 that is, for example, more than 50 degrees. Some of the magnet pack sectors 101 can be in maintained in their original deposition positions, for example, the two sectors illustrated in positions 101a congruent with target 25, while others are rotated away from the target back surface, such as the six sectors illustrated in positions 101b as retracted from the surface of the target 25. Individual magnet pack sectors 101 are provided with suitable actuators 102, which may, for example, use pneumatic or electric activation, that can move sectors 101 relative to a housing 103. The actuators 102 are represented only symbolically in FIG. 3. Appropriate actuators 102 can be of any of many available industrial products, selected from any of many vendors. The actuators 102 should have an adequate stroke, for example up to 100 mm, which should be sufficient to move magnet pack sectors 101 into a position that reduces the magnetic field at the target surface to approximately 10 percent of the original magnitude provided for sputtering deposition. For safety and control purposes, the actuators 102 may be provided with position sensors, for example, magnetic reed switches (which would need magnetic shielding from the magnet pack influence), or solid state or inductive proximity switches, all which would preferably allow for fully automatic operation. The detailed application of such actuators 102 is well known to system engineers working in the field.

Figure 4A:
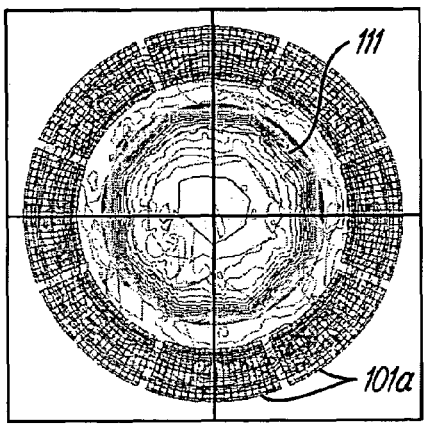
FIGS. 4A-4E are magnetic field envelope profile diagrams of the magnet pack of FIG. 3 having eight individual segment blocks, each constituting an approximately 45 degree portion of the annular magnet pack, shown in different stages of its duty cycle, with different numbers of the segments turned up to reduce the magnetic field at the target surface in given location: a) 100 percent; b) 75 percent; c) 50 percent; d) 25 percent and e) 0 percent, respectively.
Figure 4B:
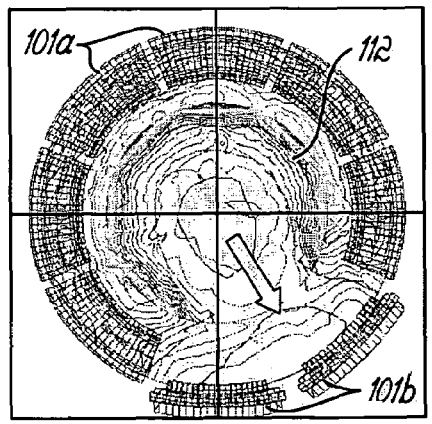
Figure 4C:
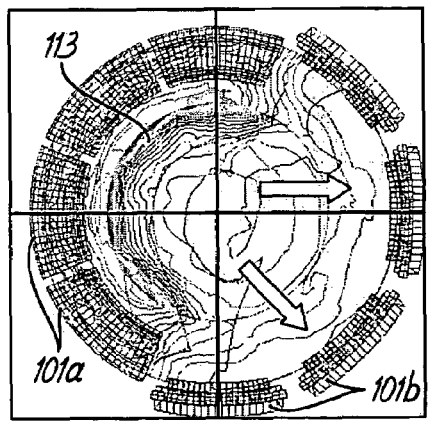
Figure 4D:
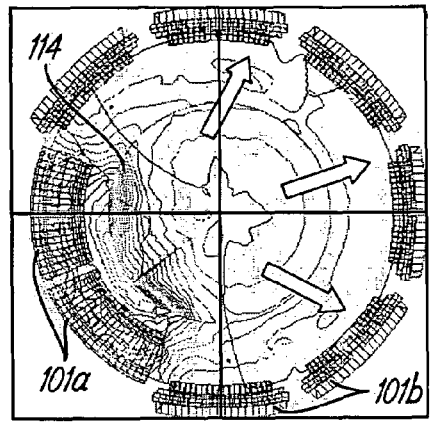
Figure 4E:
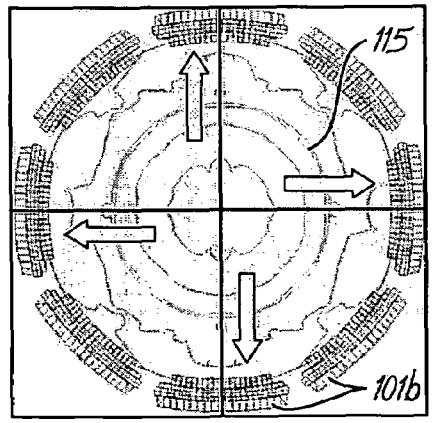
Figure 5A:
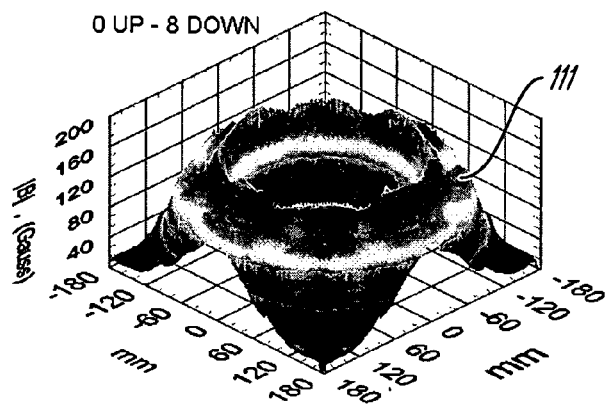
FIGS. 5A-5E are three-dimensional graphs representing the azimuthal distribution of the average magnetic field at the surface of the annular target with the magnet pack in the respective positions of FIGS. 4A-4E.
Figure 5B:
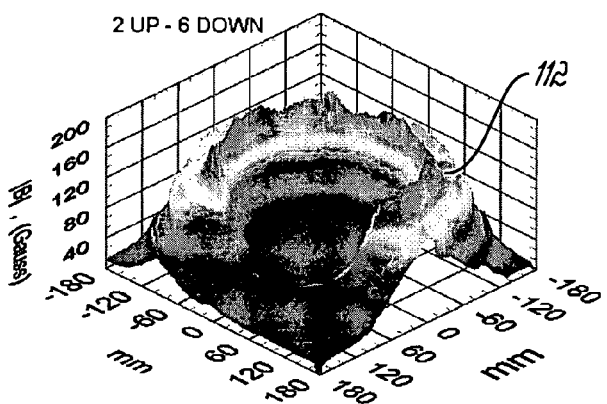
Figure 5C:
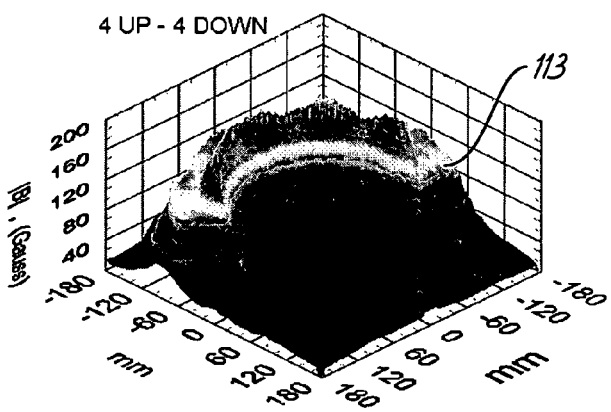
Figure 5D:
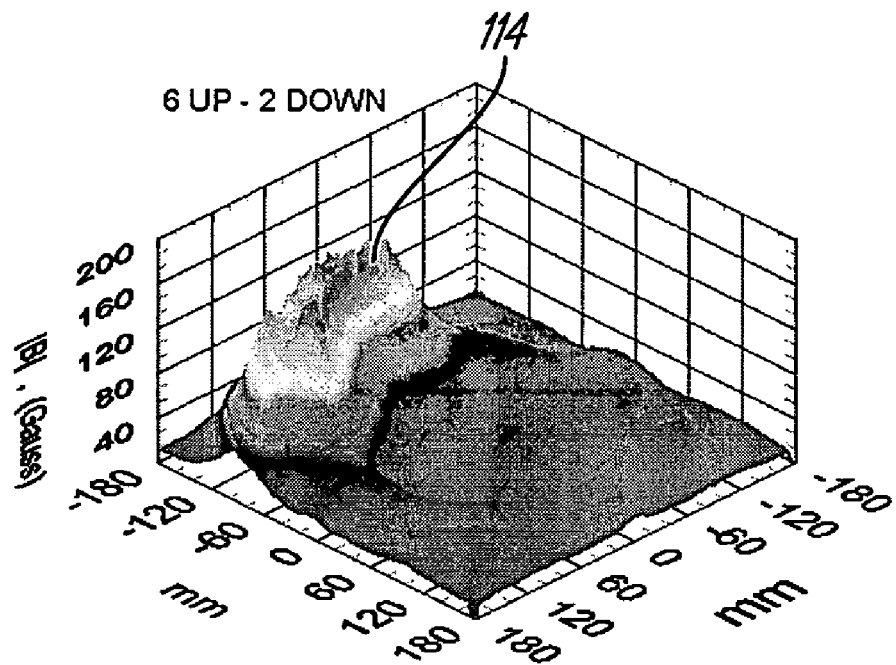
Figure 5E:
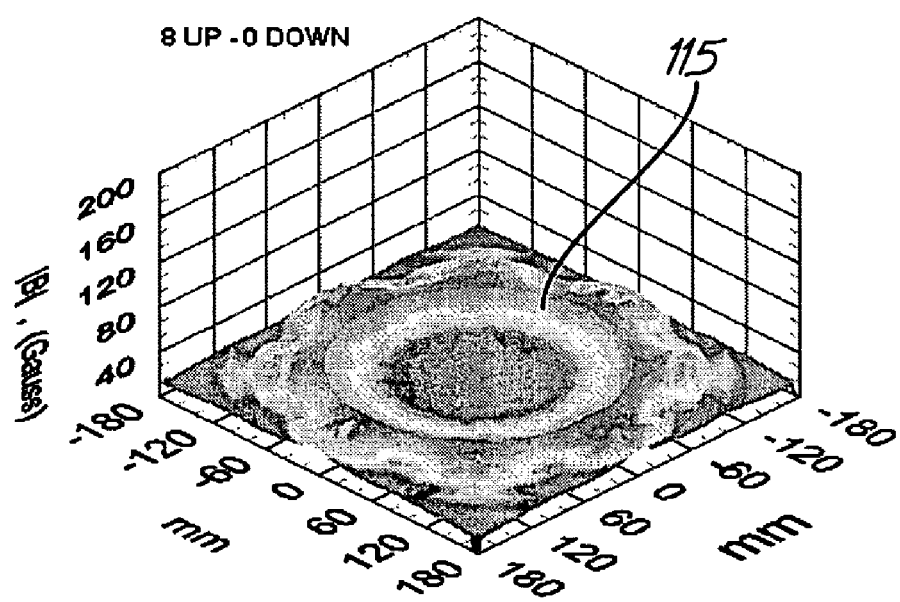

The resultant magnetic field created inside chamber 30 that interacts with the plasma has an azimuthally distributed magnitude that changes with the motion of the sectors 101, as illustrated in FIGS. 4A-E and in the respective corresponding 3D plots of FIGS. 5A-E. Moving individual magnet sectors 101 away from the target 25 can vary plasma confinement at the target surface from 0 to 100 percent of the maximum confinement that the magnet pack 34 is designed to produce: FIGS. 4A and 5A depict the field strength and pattern 111 with all sectors 101 in their positions 101a proximate the target 25, producing 100 percent of the maximum plasma confinement; FIGS. 4B and 5B depict the field strength and pattern 112 with six sectors 101 in their positions 101a proximate the target 25 and two sectors 101 in their raised positions 101b rotated away from the target 25, producing 75 percent of the maximum plasma confinement; FIGS. 4C and 5C depict the field strength and pattern 112 with four sectors 101 in their positions 101a proximate the target 25 and four sectors 101 in their raised positions 101b rotated away from the target 25, producing 50 percent of the maximum plasma confinement; FIGS. 4D and 5D depict the field strength and pattern 112 with two sectors 101 in their positions 101a proximate the target 25 and six sectors 101 in their raised positions 101b rotated away from the target 25, producing 25 percent of the maximum plasma confinement; and, FIGS. 4E and 5E depict the field strength and pattern 112 with all eight sectors 101 in their raised positions 101b rotated away from the target 25, producing nearly 0 percent of the maximum plasma confinement.

Figure 6A:
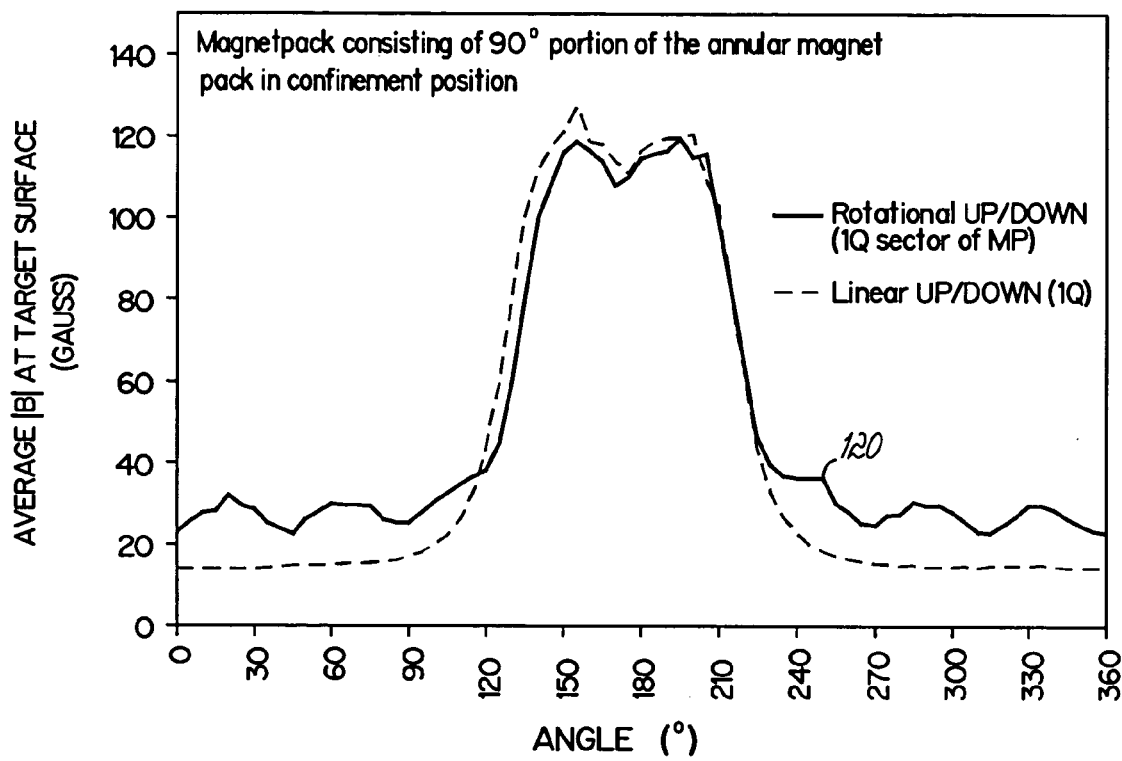
FIG. 6A is a graph illustrating the average magnetic field at the surface of the annular target with magnet pack in the position illustrated in FIG. 4D, the azimuthal magnetic field being characterized by FWHA=95 degrees.
Figure 6B:
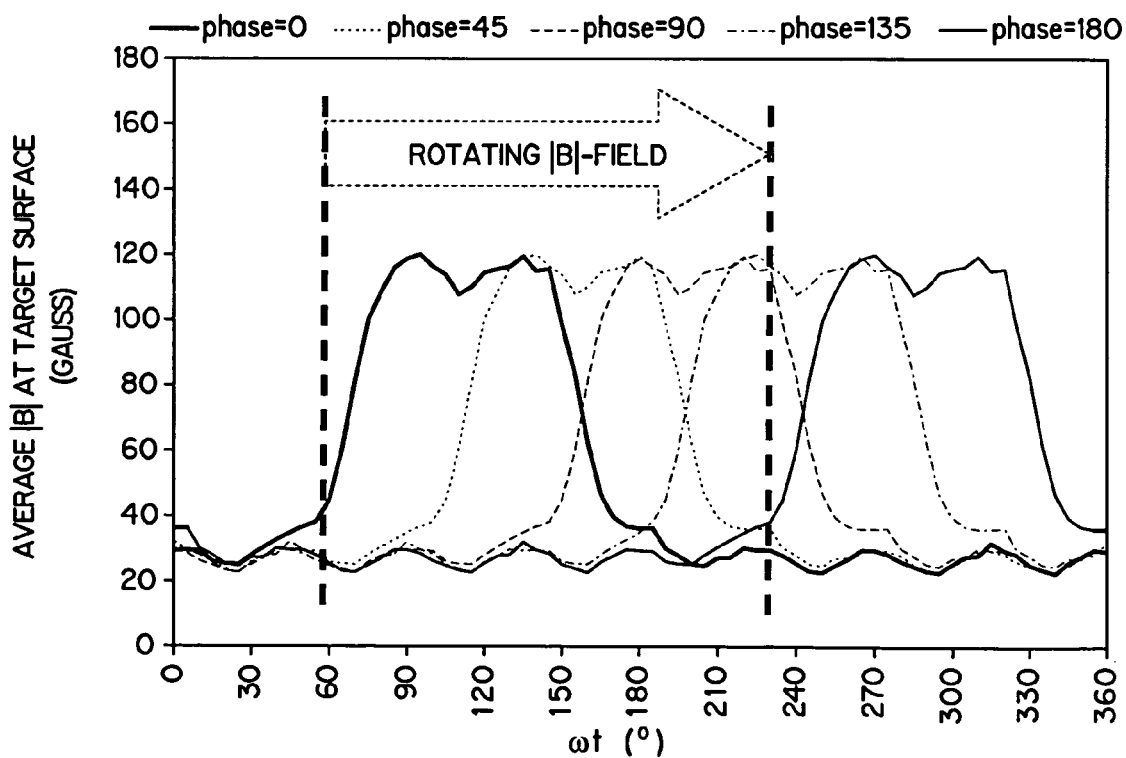
FIG. 6B is a graph, similar to FIG. 6B, illustrating the average magnetic field produced by sweeping the azimuthal distribution annularly around the target.

For example, the solid curve 120 in FIG. 6A shows a magnetic field envelope of 25 percent confinement at the target surface created by a 90 degree portion of magnet pack 34, with six segments 101 retracted (FWHA=95 degrees. The two curves show data that represent two different motion paths for the sectors. The magnetic field envelope produced by this configuration provides a reasonable sputtering rate from the target 25, maintains a high utilization erosion profile at the target surface, and reduces radial diffusion of plasma. However, the off-axis asymmetry of the magnetic field, for plasma confinement of between 25-50 percent as seen in FIGS. 4C and 4D, will generate conditions for plasma to diffuse easily in a direction of the low or zero magnetic field, thereby generating an off-axis, peaked plasma distribution profile, as shown in FIGS. 5C and 5D. By constantly changing positions of the sectors so that different sectors occupy the positions 101a and 101b, an effectively traveling magnetic field envelope is produced that moves around the target surface, which is represented by FIG. 6B. In a full cycle of the magnetic field motion, all of the target surface will have been uniformly eroded. The cumulative thickness of coating deposited on the wafer will exhibit higher uniformity across the wafer.

Figure 6C:
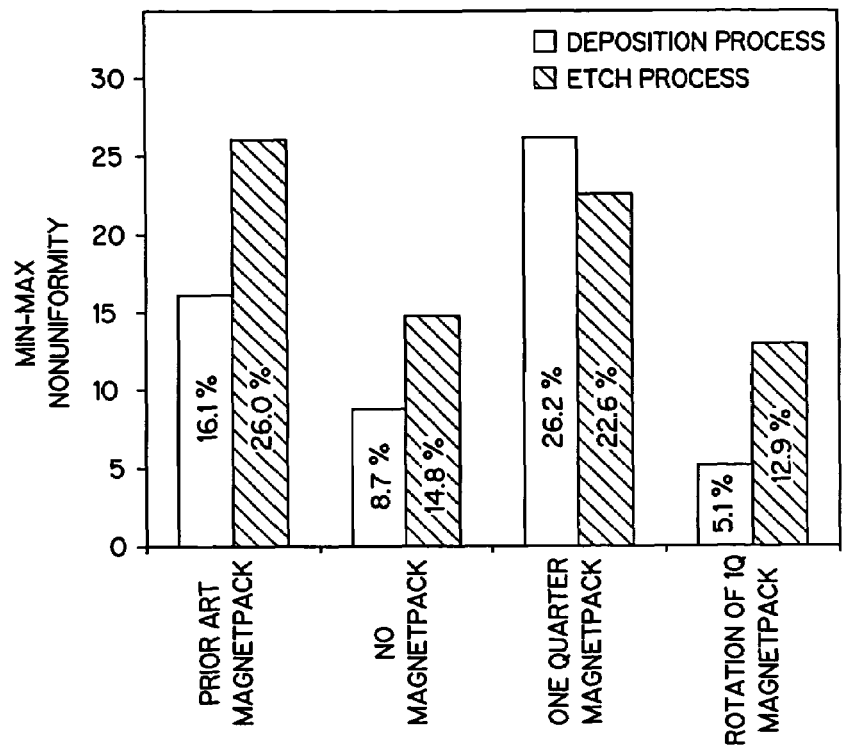
FIG. 6C is a bar graph nonuniformity of the Cu deposition and etching of a 300 mm wafer with the magnet pack in different configurations, including that of a static high utilization magnet pack, no magnet pack, one quarter section of the static magnet pack (FIG. 4D) and 360 degree rotation of one quarter section of magnet pack of FIG. 4D.

The histograms in FIG. 6C are experimental data that show an increase in minimum to maximum uniformity during a deposition process of from about 16.1 percent for the prior art to 5.1 percent with the sweeping magnetic envelope. In an etching process, the data show an increase in uniformity of from 26 percent for the prior art to 12.9 percent with the sweeping magnetic envelope. This is better uniformity than with the magnet pack totally removed, which produces uniformity of about 8.7 percent for deposition and 14.8 percent for etching. On the other hand, using the magnet pack configuration of FIG. 4D without moving the field produces 26.2 percent for deposition and 22.6 percent for etching.

Another advantage of the moveable magnet segment approach is that extensive heat load due to sputtering occurs on only a portion of the target surface at a time, such as on only about 25 or 50 percent of the target surface. Reduced heat load provides for a cooler target and would require lower DC power to achieve the same power density at target surface.

Figure 6D:
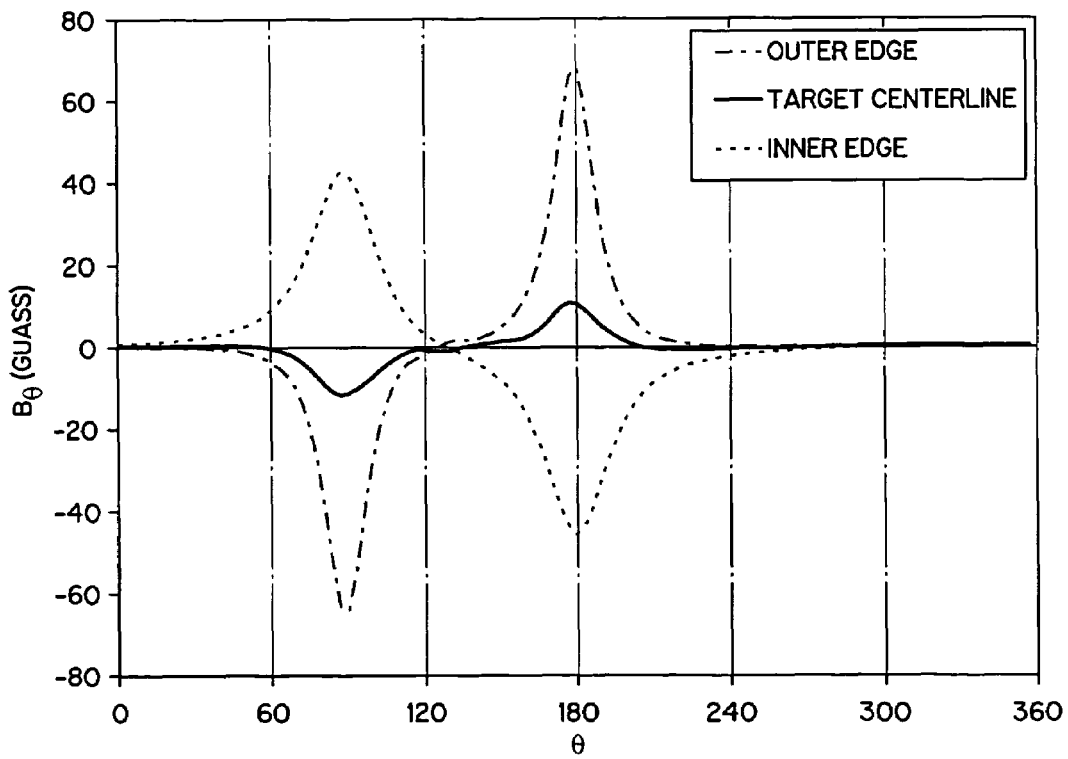
FIG. 6D is a graph of the measured azimuthal component of the magnetic field generated by the annular magnet pack in the position of FIG. 4D at different radii at the conical target surface.

By dividing magnet pack into more than eight smaller sections and then integrating the resultant etch or deposition effect by magnet movement should not give significant increase in uniformity. Rather, increase in uniformity may be due to the following factors:

1. Off-axis of plasma distribution reduces diffusion on the side of the magnet pack where the plasma is confined, and is not restricted on the side without magnetic confinement of the plasma. The non-proportional plasma losses at each sector generate off-axis plasma distribution.
2. The annular magnet pack configured to produce 100 percent plasma confinement generates azimuthal current due to the drift in E×B fields at the target surface. Leaking of the plasma current from the magnetron track occurs only due to the collisions. A magnet pack that produces only partial plasma confinement generates a magnetic field with an azimuthal component $B_\theta$ up to 50 percent of a total magnitude (see FIG. 6D), Which was not present in annular magnet pack where the value of $B_\theta$ is almost zero everywhere at the target surface. Due to this field, a leakage of plasma current from an active magnetron track occurs into the non-confined plasma, increasing local plasma density.
3. At certain configurations of the magnet pack 100, particularly those producing partial confinement as in FIGS. 4B-D, the amount of metal sputtered into the plasma is proportional to the percentage of plasma confinement. In these cases, operating at unchanged conditions (same ICP power, pressure, and DC target power), a larger ionization fraction of the metal will be achieved. Highly ionized plasma will be produced off-axis. This positively affects the feature coverage at the wafer edge making process performance more uniform with respect to center-to-edge position.

Additional advantages appear when using the moving field concept in in-situ deposition-etch processes or NND processes. Various portions of the wafer are instantly exposed to the variable ratio of the dep/etch sequence. The confinement percentage ratio and magnet pack configuration add to the process control parameters available to the operator.

Figure 7A:
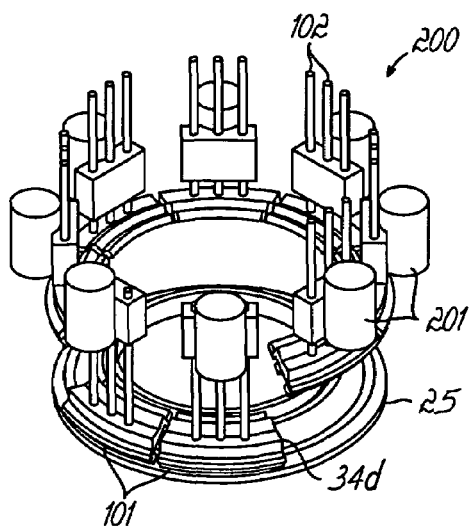
FIG. 7A is a perspective diagram of a sectored annular magnet pack of FIG. 1A configured for providing a rotating magnetic envelope inside the chamber according to a second embodiment of the present invention.

A second embodiment 200, shown in FIG. 7A, utilizes only linear motion of the individual magnet pack sectors 101, which might be easier to manufacture and may provide a more compact assembly. Linear actuators 201 may be used to provide motion of the magnet pack sectors 101, which may be supported on linear rods 202, which are connected to the yoke (see 34D in FIG. 1A) of the magnet pack assembly embodiment 200. The actuators 121 easily provide a stroke up to 100 mm, which is usually sufficient enough to reduce the magnetic field at the target surface below 10 percent of the original maximum magnitude. The body of the actuator 201 may be supported on a robust flange (not shown) or supported directly on the chamber body. For safety and control purposes, the actuators are provided with position sensors like magnetic reed switches, solid state or inductive proximity switches. The backplane of the target 25 may provide cooling channels for target. An advantage of the first and second embodiments described above is that they provide a flexible confinement percentage that can be changed in situ at any time by a control program, or even controlled within one cycle to compensate for another cause of non-uniformities (e.g., gas flow skew, coil asymmetry, etc.). Another mechanical and packaging advantage is that any connections to the target (e.g., water cooling stubs, DC power connection, sensors, etc.) do not make obstacles to the motion of the magnet pack sectors, and an effective rotating or otherwise sweeping or moving magnetic field envelope can be achieved. The magnetic field envelope of the second embodiment at 25 percent plasma confinement is shown by curve 220 in FIG. 6A.

Figure 7B:
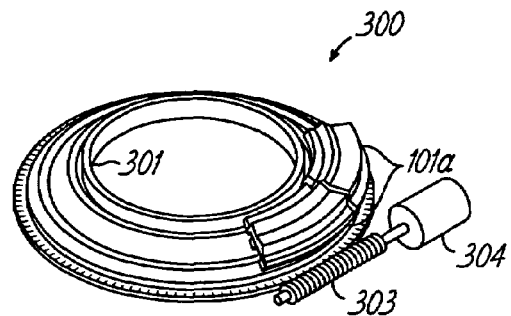
FIG. 7B is a perspective diagram, similar to FIG. 7A, of a sectored annular magnet pack of FIG. 1A configured for providing a rotating magnetic envelope inside the chamber according to a third embodiment of the present invention.

As illustrated in FIG. 7B, a third embodiment 300 excludes all sectors 101b of the magnet pack that would be distanced from the target 25 in the embodiments 100 and 200. Instead, only sectors 101a that are in plasma confinement positions are included, and these are fixed to a rotatable ring 301. Shown are two sectors 101a configured to produce from 25 to 50 percent plasma confinement, as with the configuration of FIG. 4D. The ring 302 may be installed within the magnet pack space and connected to the worm gear 303 that is driven by an electrical motor 304 to provide rotation of the magnet pack 300. In this case, all connections to the target (e.g., water cooling stubs, DC power connection, sensors, etc.) are designed so as to not interfere with rotation of the magnet pack. An advantage of the embodiment 300 is that it is very compact, easy to control to produce a moving magnetic field envelope at the target surface.

Figure 7C:
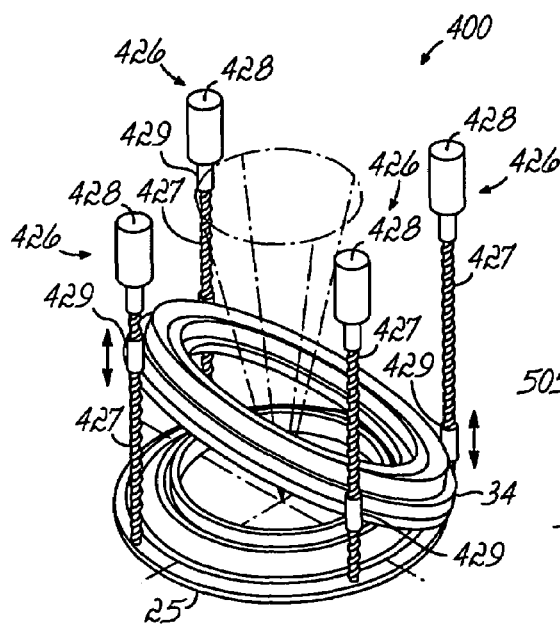
FIG. 7C is a perspective diagram, similar to FIGS. 7A-7B, of a sectored annular magnet pack of FIG. 1A configured for providing a rotating magnetic envelope inside the chamber according to a fourth embodiment of the present invention.
Figures 8A, 8B, 8C:
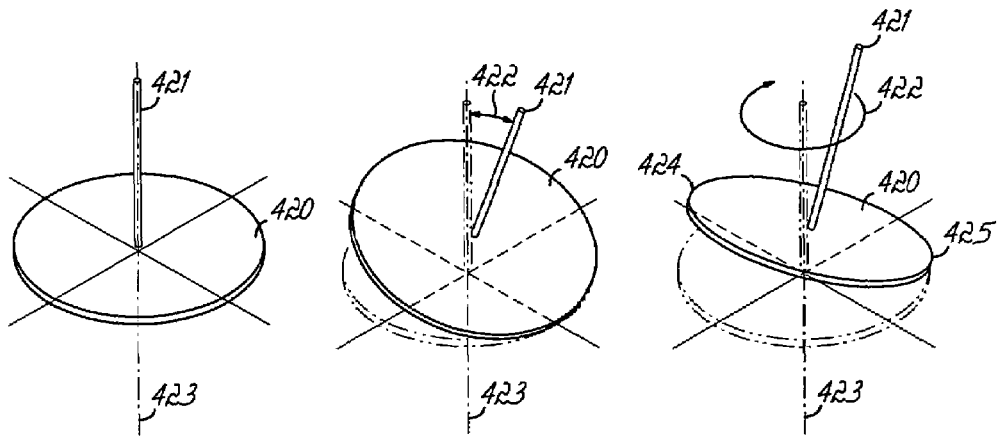
FIGS. 8A-8C are sequential diagrams illustrating the gyro-motion of the magnet pack (which, for simplicity, is shown as a disk).

A fourth embodiment 400 uses a full size magnet pack annular magnet 34 that is moving in a specific manner, for example, wobbled, as illustrated in FIG. 7C. A character of this motion is easily understood from the illustration in FIG. 8A-C. This is demonstrated by representing the magnet 34 of the assembly 400 as a disc 420 with a bar 421 attached to its center and normal thereto (FIG. 8A). The bar 421 may be reoriented so that the disc 420 is tilted into the position shown in FIG. 8B, to an angle 422 of between 15 and 20 degrees, for example. The tip of the bar 421 is then rotated around a vertical axis 423, which wobbles annular magnet 34 (disc 420) to bring one point on the rim 424 of the disc 420 away from the target while the diametrically opposite point 425 on the rim remains proximate the target, as shown in FIG. 8C.

Figure 1A:
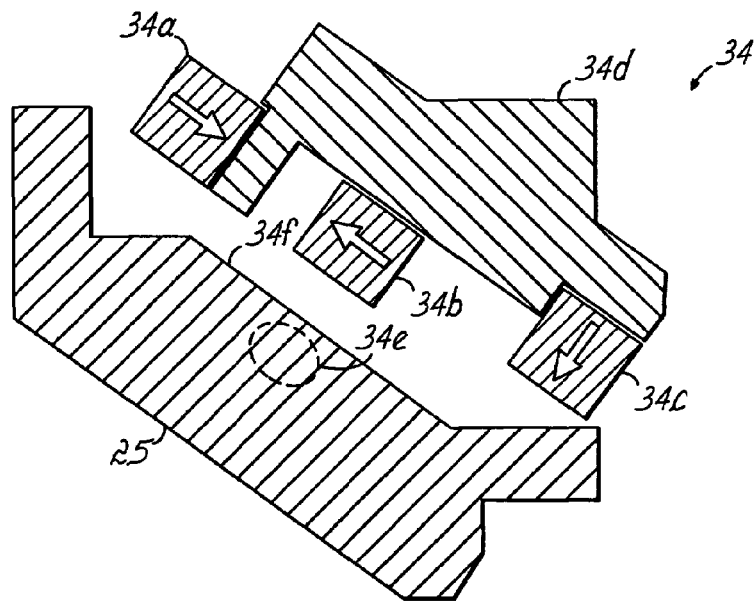
FIG. 1A is a an enlarged cross-sectional view of the magnetron magnet pack of the circled portion of FIG. 1.
Figure 9:
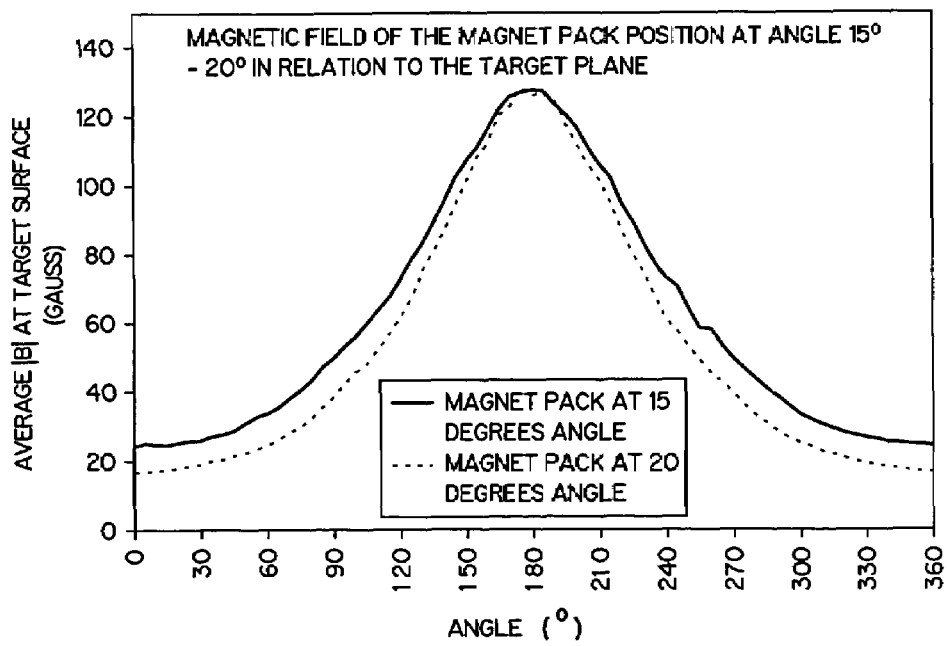
FIG. 9 is a graph illustrating the average magnetic field at the surface of the annular target with the magnet pack having the motion of FIGS. 8A-8C, the azimuthal magnetic field being characterized at a tilting angle of 15 degrees by FWHA=140 degrees, and by FWHA=115 degrees at a tilting angle of 20 degrees.

Applying this type of the motion to the full size annular magnet pack, one can observe a traveling magnetic field envelope at the target surface due to the rotation of the virtual touching point 425 and the diametrically opposed point 424 that is distanced from the target. The magnetic field envelope, using the same magnet pack configuration as was shown in FIG. 1A, is shown in FIG. 9. The FWHA is from 115 degrees to 140 degrees, for tilting angles of 20 degrees and 15 degrees, respectively. The actual embodiment is embodiment 400 shown in FIG. 7C. There are several ways to produce this motion, which may be referred to as gyro-motion. One suitable preferred configuration is shown. The profile of the yoke 34d of the magnet will be shallower than that shown in FIG. 1A to facilitate congruency of the magnet with the target surface when the magnet pack is in a tilted position. For example, the cross-section of FIG. 1A can be maintained relative to that of the target for the portion of the magnet assembly that is proximate the target when the plane of the magnet pack is inclined at the tilting angle. Other arrangements can be achieved with mechanical modeling.

To move the magnet, three or four actuators 426 may be used (while other numbers are possible but may be more difficult to control), each including a motor 428, a worm gear 427 and a coupling 429. The actuator 426 is attached by the worm gear 427 to the magnet pack 34, each providing linear motion in vertical direction. The worm gears 427 are driven by motors 428 attached through flexible ball couplings 429 and which are driven in phase delay. Other motion algorithms can be developed to create more complex motions for particular processes. Amplitude and rotational speed of the magnetic field envelope is determined by the stroke of the worm gears 427, speed of the motors 428 and the phase between the individual motors 428.

Any connections to the target (water cooling stubs, DC power connection, sensors, etc.) should not be obstacles to the motion of the magnet pack sectors. Additional tolerance and increased cross-section of openings in the magnet pack might be desirable to avoid interference with such connections, but, nevertheless, an effective rotating magnetic field envelope can be achieved in this manner.

Figure 7D:
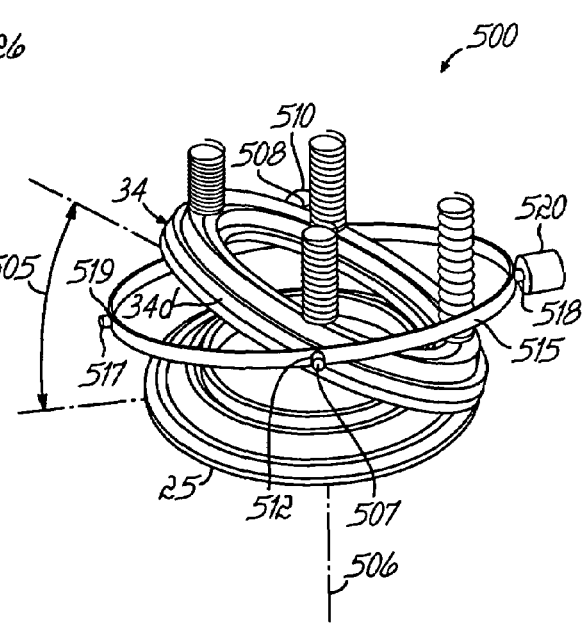
FIG. 7D is a perspective diagram, similar to FIGS. 7A-7C, of a sectored annular magnet pack of FIG. 1A configured for providing a rotating magnetic envelope inside the chamber according to a fifth embodiment of the present invention.

A fifth embodiment is illustrated in FIG. 7D, which shows a magnet pack 500, also having a magnet assembly 34 as described above. The embodiment 500 is provided with a mechanism for producing a motion similar to that of embodiment 400 described above. This embodiment is technically simple, reliable and inexpensive. In the embodiment 500, a gyro-motion of the magnet pack 34 is produced. The magnet pack 34 is provided with a mechanism in which the yoke 34*d* is supported behind the target 25 at a distance that is approximately 1-2 inches when the yoke 34*d* has an outer diameter of approximately 16 inches. This position allows for tilting angle 505 of the yoke 34*d* relative to the target 25 of from about 15 degrees to about 30 degrees around the center line 506 of the yoke and target. Yoke 34*d* may be attached to diametrically aligned shafts 507 and 508. The shaft 508 may be attached to motion actuator 510, for example, a stepping motor. The position of the shaft 508 may be fixed by a bearing 512, which may be attached to a gyro-ring 515. The profile of the yoke 34*d* may be reduced from that of FIG. 1A to allow it to be congruent with the target surface when the magnet pack 34 is in a tilted position.

Another two diametrically aligned shafts 517 and 518 may be provided, which may be fixed to the gyro-ring 515. The position of shaft 517 may be fixed by a bearing 519, which is attached to a base plate or housing (not shown) that is fixed relative to the chamber wall. The shaft 518 is attached to the rotational motion actuator and motor 520, firmly attached to the module base plate.

Action of the actuator 510 provides motion of the magnet pack 34 around the axis of the shafts 507 and 508, while action of the actuator 520 provides motion of the magnet pack 34 around the axis of the shafts 517 and 518. The combination of the motions produced by actuators 510 and 520 results in a gyro-motion of the magnet pack 34 and a sweeping magnetic field envelope about the centerline 506, around the surface of the target 25. Springs 531-534 may be provided to help the actuators 510 and 520 overcome gravitational or other forces. The springs 531-534 may, for example, be compressed between the chamber wall or apparatus housing (not shown) and the magnet pack yoke 34*d*.

Generally, the actuators 510 and 520 are driven at a phase delay of one relative to the other. This is achieved by starting from the initial position when magnet pack 34 is in a balanced position in plane parallel to the target plane and, for example, advancing one of the actuators 510, 520 an amount of 90 degrees relative to the other, then starting the process at this point. Other algorithms can be developed to create more complex motions for particular processes. Amplitude and rotational speed of the magnetic field envelope is determined by motor speed and phase between individual motors. Several revolutions per process step help insure uniformity, while high rotational speed is not usually necessary.

Connections to the target 35, such as water cooling stubs, DC power connection, sensors, etc., don't obstruct the motion of the magnet pack 34 with this embodiment. Additional tolerance and increased cross-section of openings in magnet pack yoke 34*d* help avoid interference with such connections, but nevertheless, an effective sweeping magnetic field envelope still can be achieved. A magnet pack assembly 500 with electrically driven actuators 510, 520 can be easily integrated into the controller network of the apparatus (see FIG. 2).

Advantages appear when using the embodiments described above in an in-situ deposition-etch process or NND (no-net-deposition) process. In such a process, the various portions of a wafer are instantly exposed to the variable ratio of the dep/etch sequence. The plasma-confinement percentage or "duty cycle" ratio, as it may be called, and the magnet pack configuration add to the process control parameters available of the operator.

Those skilled in the art will appreciate that deletions, additions and modifications can be made to the above described embodiments without departing from the principles of the invention.

Therefore, the following is claimed:

1. An ionized physical deposition method comprising:
   sealing a substrate within a chamber of a processing apparatus;
   performing a deposition-etch process to deposit a film of material from a sputtering target on surfaces of high aspect ratio submicron features on the substrate;
   while performing the deposition-etch process, sweeping around a sputtering surface of the sputtering target a magnetic field that produces plasma confinement over the sputtering surface with relatively higher plasma confinement over only a portion of the sputtering surface of the sputtering target, the sweeping of the magnetic field being achieved by rotating a magnet assembly having magnets moveably mounted thereon about an axis of the sputtering target; and
   while sweeping the magnetic field around the sputtering surface, varying parameters of the magnetic field by changing the position of one or more magnets relative to the assembly as the assembly rotates about the axis so that the magnetic field changes with the angular position of the rotating magnet assembly;
   the changing of the position of the one or more magnets as the assembly rotates being controlled such that the target is sputtered non-uniformly in a way that compensates for at least some azimuthal non-uniformities on the substrate in the deposition-etch process so as to improve overall azimuthal uniformity of the process around the substrate.

2. The method of claim 1 further comprising:
   inductively coupling a high density plasma into a space within the chamber to produce ions of coating material to be deposited onto the substrate during the deposition portion of the deposition-etch process.

3. The method of claim 2 for depositing coatings on semiconductors having submicron, high aspect ratio wherein the performing of the ionized physical deposition process includes performing the deposition portion of the process at a pressure of at least approximately 30 mToff.

4. The method of claim 1 wherein:
   the sweeping includes rotating the magnetic field about a centerline of the target surface.

5. The method of claim 1 wherein:
   the sweeping includes moving the magnetic field through a plurality of cycles with the magnetic field configured to produce uniform deposition within each cycle.

6. An ionized physical vapor deposition apparatus comprising a controller configured to operate the apparatus according to the method of claim 1, and further comprising:
   a permanent magnet assembly rotatably mounted behind the sputtering target configured to produce the magnetic field, the magnet assembly having one or more permanent magnets moveably mounted thereto; and one or more actuators connected between the rotatable magnet assembly and the respective one or more moveably mounted permanent magnets, the actuators being responsive to the controller and operative to cause the field to sweep around the sputtering surface of the sputtering target.

7. The apparatus of claim 6 wherein the controller is programmed to move the one or more magnets to change the size of said portion of the sputtering surface.

8. The apparatus of claim 6 wherein:
the permanent magnet assembly includes a plurality of magnet sectors; and
the one or more actuators includes a plurality of actuators, each linked to a different one of the sectors, each responsive to the controller, and each operable to move the sectors so as to cause the field to sweep around the sputtering surface of the sputtering target.

9. The apparatus of claim 6 wherein:
the permanent magnet assembly includes an annular magnet assembly having magnets around the circumference of the magnet assembly; and
the one or more actuators is linked to a magnet pack and responsive to the controller, and is operable to move the magnet assembly in a gyro-motion so as to cause the field to sweep around the sputtering surface of the sputtering target.

10. An ionized physical vapor deposition apparatus comprising:
a vacuum chamber operable to perform ionized physical vapor deposition on a substrate therein over a pressure range of from not more than approximately 1 mTorr to over 30 mTorr;
a sputtering target having an axis centered on an axis of the sputtering chamber and a sputtering surface at one end of the chamber;
a substrate support at an opposite end of the chamber from the sputtering target;
an ICP source operable to inductively couple RF energy into a plasma in a process volume within the chamber to form a high density plasma therein;
a magnet pack behind the sputtering target and rotatable about the axis of the sputtering target so as to sweep a magnetic field around the surface of the sputtering target with a field strength that varies with its position on the sputtering surface as the field sweeps around the sputtering surface, the magnet pack having one or more magnets moveably mounted thereon about an axis of the sputtering target; and
a controller programmed and configured to control the magnet pack to change the position of at least one of the one or more magnets relative to the magnet pack as the magnet pack rotates about the axis of the target so that the magnetic field changes with the angular position of the rotating magnet pack to vary the field strength azimuthally as a function of the azimuthal position of the field on the sputtering surface.

11. The apparatus of claim 10 wherein:
the controller is further programmed to operate the apparatus sequentially, with a single substrate in the chamber, without opening the chamber, in a plurality of modes including a deposition mode, by sputtering material from a sputtering target into the plasma to ionize the material and depositing the material onto the substrate, and an etch mode, by etching material from the substrate with ions from the plasma, the modes being performed while sweeping the magnetic field around the surface of the sputtering target; and
the deposition mode is carried out at pressures greater than 30 mTorr, and the etch mode is carried out at pressures less than 10 mTorr.

12. The apparatus of claim 10 wherein:
the magnet pack is configured to produce a magnetic field that confines the plasma to only a portion of the sputtering surface of the target and to sweep the field by moving said portion around the said surface of the target.

13. The apparatus of claim 12 wherein:
the controller is configured to move at least one of the one or more magnets of the magnet pack to facilitate either a change of the size of said portion of the said surface or to change the strength of the magnetic field in said portion as a function of the angular position of said portion about the axis of the sputtering target.

14. The apparatus of claim 10 further comprising:
at least one actuator configured to move the magnet pack or one or more magnets thereof, in response to the controller, so as to cause the field to sweep around the sputtering surface of the sputtering target.

15. The apparatus of claim 14 wherein:
the magnet pack includes a plurality of moveable magnet sectors; and
the at least one actuator includes a plurality of actuators, each linked to a different one of the sectors, each responsive to the controller, and each operable to move a sector so as to cause the field to sweep around the sputtering surface of the sputtering target.

16. The apparatus of claim 14 wherein:
the permanent magnet pack includes an annular magnet assembly having the one or more magnets extending around the circumference of the magnet pack; and
the at least one actuator is linked to a magnet pack and responsive to the controller, and is operable to move the magnet pack in a gyro-motion so as to cause the field to sweep around the sputtering surface of the sputtering target.

17. The apparatus of claim 10 wherein:
the magnet pack is configured to produce a magnetic field that concentrates a plasma in a volume over a portion of the surface of the sputtering target and sweeps the volume over the sputtering surface of the sputtering target.

18. The apparatus of claim 10 wherein the magnet pack is configured to vary the magnetic field in a way that improves the uniformity of the plasma.

19. The apparatus of claim 10 wherein the controller is configured to control the magnet pack to vary the magnetic field with its position so as to improve the uniformity of the plasma.

* * * * *

UNITED STATES PATENT AND TRADEMARK OFFICE
CERTIFICATE OF CORRECTION

PATENT NO.        : 7,556,718 B2                                                     Page 1 of 1
APPLICATION NO.   : 10/873908
DATED             : July 7, 2009
INVENTOR(S)       : Jozef Brcka It is certified that error appears in the above-identified patent and that said Letters Patent is hereby corrected as shown below:

In Column 2, line 52, "to inductively coupling RF energy" should read -- to inductively couple RF energy --.

In Column 3, lines 17-18, "magnet pack may in include" should read -- magnet pack may include --.
In Column 3, line 32, "FIG. 1A is a an enlarged" should read -- FIG. 1A is an enlarged --.
In Column 3, line 59, "similar to FIG. 6B" should read -- similar to FIG. 6A --.
In Column 3, line 62, "bar graph nonuniformity" should read -- bar graph illustrating nonuniformity --.

In Column 5, lines 48-49, "over the all target" should read -- over all the target --.

In Column 6, line 8, "improve and affect" should read -- improve and effect --.

In Column 7, line 39, "can be in maintained" should read -- can be maintained --.

In Column 8, line 28, "(FWHA=95 degrees." should read -- (FWHA=95 degrees). --.

In Column 9, line 17, "(see FIG. 6D), Which was" should read --(see FIG. 6D), which was --.

In Column 12, line 10, "available of the operator." should read -- available to the operator. --.

In Claim 3, Column 12, line 53, "approximately 30 mToff." should read -- approximately 30 mTorr. --.

Signed and Sealed this

Twenty-third Day of March, 2010

David J. Kappos
*Director of the United States Patent and Trademark Office*